United States Patent [19]
Saito et al.

[11] Patent Number: 5,731,172
[45] Date of Patent: Mar. 24, 1998

[54] RECOMBINANT ADENOVIRUS AND PROCESS FOR PRODUCING THE SAME

[75] Inventors: Izumu Saito; Yumi Kanegae, both of Tokyo, Japan

[73] Assignee: Sumitomo Pharmaceuticals Company, Ltd., Osaka, Japan

[21] Appl. No.: 302,312

[22] Filed: Sep. 8, 1994

[30] Foreign Application Priority Data

Mar. 9, 1994 [JP] Japan ..................... 6-066813

[51] Int. Cl.$^6$ ............... C12N 15/64; C12N 15/66
[52] U.S. Cl. ............... 435/91.42; 435/172.3; 435/320.1; 435/369
[58] Field of Search ............... 435/69.1, 91.4, 435/91.42, 91.33, 172.1, 172.3, 320.1, 366, 369, 91.41

[56] References Cited

FOREIGN PATENT DOCUMENTS

| 0220009 | 4/1987 | European Pat. Off. . |
|---|---|---|
| 0300422 | 1/1989 | European Pat. Off. . |

OTHER PUBLICATIONS

Saito, et al "Construction of Nondefective Adenovirus Type 5 Bearing a 2.8 Kilobase Hepatitis B Virus DNA . . . ," *Journal of Virology*, vol. 54, No. 3, pp. 711–719, Jun. 1985.
Sharp, et al "The Infectivity of Adenovirus 5 DNA–Protein Complex," *Virology*, 75, 442–456 (1976).
Gu et al., "Deletion of DNA Polymerase . . . Targeting," *Science*, vol. 265, Jul. 1, 1994, pp. 103–106.
Anton et al., "Site Specific Recombination Mediated . . . Expression," *Journal of Virology*, Aug. 1995, pp. 4600–4606.
*First Annual Meeting 1995 Japanese Society of Gene Therapy*, Program and Abstract, May 21, 1995, Kanagae et al, "Application of Cre/LoxP System to Adenovirus Vector".
Kanegae et al., "Efficient Gene Activation . . . Recombinase," Nucleic Acids Research, vol. 23, No. 19, pp. 3816–3821 (1995).
Bergemann et al., "Excision of Specific DNA . . . Recombination," Nucleic Acids Research, vol. 23, No. 21, pp. 4451–4456 (1995).
The 43rd Annual Meeting of the Society of Japanese Virologists, (Sep. 29, 1995), 2016, p. 126.
*The Second Brain Tumor Gene Therapy Meeting*, Feb. 3 and 4, 1995, "Adenovirus Vector".
Ghosh–Choudhury et al., "Protein IX, A Minor Component of the Human Adenovirus Capsid, is Essential for the Packaging of Full Length Genomes", EMBO J., vol. 6, No. 6, pp. 1733–1739, 1987.
K.L. Berkner, "Expression of Heterologous Sequences in Adenoviral Vectors", Current Topics in Microbiol. and Immunol., vol. 158 1992, pp. 39–66.
Saito et al., "Adenovirus Vector", The 41$^{st}$ General Meeting: The Society of Japanese Virologists (1993).
Kanegae et al., "Adenovirus Vector and Gene Therapy", Experimental Medicine, vol. 12, No. 3 (1994).
Kanegae et al., Experimental Medicine Supplemental Volume, Biomanual Series 4, pp. 43–58 (1994).
Niwa et al, "Efficient Selection for High–Expression Transfectants with a Novel Eukaryotic Vector," Gene, 108, pp. 193–200 (1991).
Engelhardt et al, "Direct Gene Transfer of Human CFTR Into Human Bronchial Epithelia of Xenografts with El–Deleted Adenoviruses," Nature Genetics, vol. 4, pp. 27–34 (May 1993).

*Primary Examiner*—David Guzo
*Attorney, Agent, or Firm*—Sughrue, Mion, Zinn, Macpeak & Seas, PLLC

[57] ABSTRACT

Disclosed are a recombinant adenovirus bearing a DNA sequence encoding a desired foreign polypeptide, and a hybrid promoter (CAG promoter) comprising a cytomegalovirus enhancer, a chicken β-actin promoter, a rabbit β-globin splicing acceptor and a polyA sequence, a process for production thereof, as well as use thereof for in genetic treatment. The recombinant adenovirus effectively expresses the foreign polypeptide in a wide range of animal cells.

6 Claims, 2 Drawing Sheets

RECOMBINANT ADENOVIRUS AND PROCESS FOR PRODUCING THE SAME

BACKGROUND OF THE INVENTION

1. Field of the Invention

The present invention relates to a recombinant adenovirus bearing a hybrid promoter (CAG promoter) comprising a cytomegalovirus enhancer, a chicken β-actin promoter, a rabbit β-globin splicing acceptor and a polyA sequence, and a DNA sequence encoding a desired polypeptide. The present invention also relates to a process for producing the recombinant adenovirus and use thereof, particularly, use thereof in gene therapy.

2. Related Art Statement

Researches on adenovirus have been focused intensively on its use as a vector in experiments for transducing foreign genes, since an adenoviral vector shows a transduction efficiency of almost 100% in a variety of animal cells. In addition, the adenoviral vector has been considered to be highly effective as a vector, because the introduced foreign gene can be examined for its functions under the condition that the transduced cells are not killed, and because animal species available as a host cell are extended over a wide range including mouse and rat.

The adenovirus, however, was really valued for its use as a vector, only after a genetic treatment using an adenoviral vector for patients with cystic fibrosis had started in America in 1992 (Nature Genetics, Vol. 3, 1–2, 1993) and, the adenoviral vector had been shown to be effective in the expression method in a nervous system in 1993 (Science, Vol. 259, 988–990, 1993; Nature Genet., Vol. 3, 219–223, 1993, ibid., Vol. 3, 224–228, 1993, ibid., Vol. 3, 229–234, 1993) and thus an application of an adenoviral vector to gene therapy had been extensively suggested. Nowadays, it has thus been shown that an adenoviral expression vector achieves almost 100% transduction efficiency in many differentiated and non-differentiated cells including those in a nervous system and also enables an expression of a gene after direct infusion or administration thereof to animal body. It has therefore highly expected to apply an adenoviral vector to gene therapy.

As a viral vector for transduction, a retrovirus has been frequently employed heretofore. However, this virus can be transduced only into mitotic cells and integrated into chromosomes of host cells. It is therefore considered that a retrovirus would cause a significant problem in a genetic treatment and would be difficult to be applied widely in a gene therapy.

Unlike retrovirus, adenovirus is advantageous in that the adenovirus lacks any positive mechanism for integration into chromosome and enables the transduction of a gene even in cells at the resting phase. Therefore, the adenovirus is considered to be applicable over an extremely wide range of host cells, suggesting that gene therapy involving an adenovirus would be established as a major technique in the near future.

Adenovirus is originally known to cause cold conditions in humans. Therefore, there is a concern that administration of adenovirus in a large dose might invite inflammation. In fact, at the initial clinical stage, the attempt of gene therapy using an adenovirus by Crystal's group was said to be temporarily interrupted by the side effect of pneumonia in a patient who was administered a large dose of adenovirus to the lung. Observation was made also in experiments using cultured cells that vital infection in a high dose caused side effects attributable directly to virions, e.g., cells become round and detached in the case of adherent cells. These observations cast a significant doubt that side effects accompanied by administration of viral solution in a high dose might be caused in a practical therapy. It is therefore necessarily required to provide a combination with a promoter exhibiting a high expression level so as to ensure an expression at a sufficient level using a vital solution in a low dose. This approach is considered key to solve the foregoing problems in applying adenovirus to gene therapy.

In recent years, with advanced genetic recombination techniques, enormous progress has been seen in the production of valuable substances utilizing such a technique. Where a foreign gene is expressed by a genetic recombination technique, an appropriate host cell and an expression vector bearing a promoter for expressing the foreign gene are used. As an expression system using animal cells as host cells, many systems using animal viral gene promoters and animal cell gene promoters have been reported. Representative examples of the animal virus promoters include SV40 early promoter, adenovirus major late promoter, and the like. Typical examples of the animal cell gene promoters include thymidine kinase gene promoter, metallothionein gene promoter, immunoglobulin gene promoter, and the like. However, the activity assessment of these promoters has been performed only with established cells during the course of active division and having a high efficiency in a gene introduction by a calcium phosphate method, DEAE-dextran method, or electroporation method. Examples of such established cells may include mouse-derived L cells, hamster-derived CHO and African green monkey-derived COS cells. Thus, any study for promoter activities has not been made on differentiated cells. An expression in differentiated cells, e.g., nerve cells, muscle cells, liver cells or blood cells is important in gene therapy.

SUMMARY OF THE INVENTION

The present inventors have paid attention to the fact that adenovirus which has been barely used for gene transduction can infect cells ubiquitously in the resting phase, and thus considered that an adenovirus having a potent promoter integrated in the genome thereof would enable the expression of a gene in animal cells over a wide range. Therefore, recombinant adenoviruses bearing a variety of potent promoters have been prepared and examined for a gene expression in various host cells. As a result, the inventors have successfully produced an adenovirus showing a potent promoter activity which achieves gene expression in almost all cells. Based on the finding, further investigations have been made to accomplish the present invention.

An object of the present invention is to provide a recombinant adenovirus having a promoter exhibiting a potent activity over a wide range of animal cells, particularly a recombinant adenovirus further having a nucleotide sequence encoding a desired foreign polypeptide, more particularly, a recombinant adenovirus for use in gene therapy in which a human defective gene has been inserted.

Another object of the present invention is to provide a process for producing such a recombinant adenovirus in a simple manner.

That is, the present invention is characterized by the following features:

(1) A recombinant adenovirus bearing in the genome thereof a nucleotide sequence encoding a desired foreign polypeptide and a hybrid promoter (CAG promoter) comprising a cytomegalovirus enhancer, a chicken β-actin promoter, a rabbit β-globin splicing acceptor and a polyA sequence.

(2) A recombinant adenovirus according to the above (1), wherein said adenovirus genome is deleted of at least 1.3 to 9.3% segment including E1A gene region.

(3) A recombinant adenovirus according to the above (2), wherein said nucleotide sequence encoding a desired foreign polypeptide and said CAG promoter are inserted into the E1A-deleted gene region.

(4) A recombinant adenovirus according to the above (3), wherein said adenovirus genome is deleted of at least 79.6 to 84.8% segment including E3 gene region.

(5) A recombinant adenovirus according to any one of the above (1) through (4), wherein said nucleotide sequence encoding a desired foreign polypeptide and said CAG promoter are inserted into the genome in an orientation to the left hand.

(6) A recombinant adenovirus according to any one of the above (1) through (5), wherein said nucleotide sequence encodes a desired foreign polypeptide which has a property that, when the polypeptide is expressed under control of CAG promoter in a natural host cell, the expressed polypeptide is secreted into the culture medium.

(7) A recombinant adenovirus for use in gene therapy bearing CAG promoter.

(8) A recombinant adenovirus bearing in the genome thereof a nucleotide sequence encoding a desired foreign polypeptide and a foreign promoter which are inserted into the genome in an orientation to the left hand.

(9) A recombinant adenovirus according to the above (8), wherein said adenovirus genome is deleted of at least 1.3 to 9.3% segment including E1A gene region.

(10) A recombinant adenovirus according to the above (9), wherein said nucleotide sequence encoding a desired foreign polypeptide and said promoter are inserted into the E1A-deleted gene region.

(11) A recombinant adenovirus according to the above (10), wherein said adenovirus genome is deleted of at least 79.6 to 84.8% segment including E3 gene region.

(12) A process for producing a recombinant adenovirus having an expression unit inserted in the genome which comprises the steps of:

mixing a cosmid constructed by deleting at least 1.3 to 9.3% segment including E1A gene region in the adenovirus genome and inserting the expression unit into the E1A-deleted gene region, with an adenovirus DNA-terminal protein complex digested with a restriction enzyme at 3 to 10 sites in the left end of the adenovirus genome; and transfecting with the resulting mixture a cell line which expresses the E1A gene.

(13) A process according to the above (12), wherein said cell line is a human fetal kidney-derived cell line.

(14) A process according to the above (12), wherein said expression unit comprises a nucleotide sequence encoding a desired foreign polypeptide and CAG promoter comprising a cytomegalovirus enhancer, a chicken β-actin promoter, a rabbit β-globin splicing acceptor and a polyA sequence.

(15) A process according to the above (12), wherein said restriction enzyme is EcoT22I or, NsiI or AvaIII having the same recognition site as that of EcoT22I.

(16) A process according to the above (12), wherein said expression unit is inserted into the genome in an orientation to the left hand.

(17) A process according to the above (12), wherein each of the adenovirus genome in said cosmid and said adenovirus DNA-terminal protein complex is deleted of at least 79.6 to 84.8% segment including E3 gene region.

DETAILED DESCRIPTION OF THE INVENTION

Figure 1:
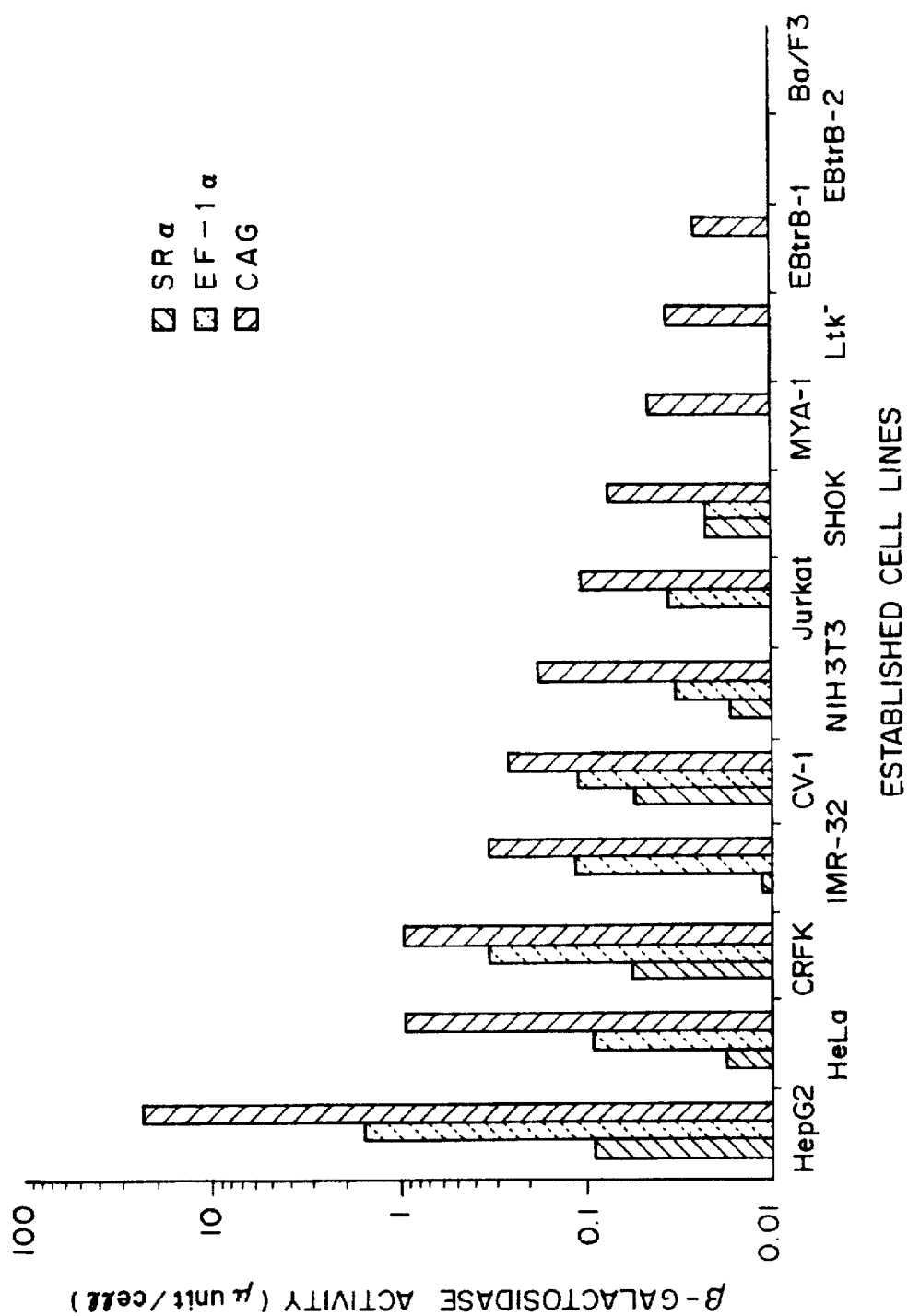
FIG. 1 shows the effect of various promoters on the expression of LacZ gene in various cell lines by recombinant adenoviruses having these promoters inserted therein.
Figure 2:
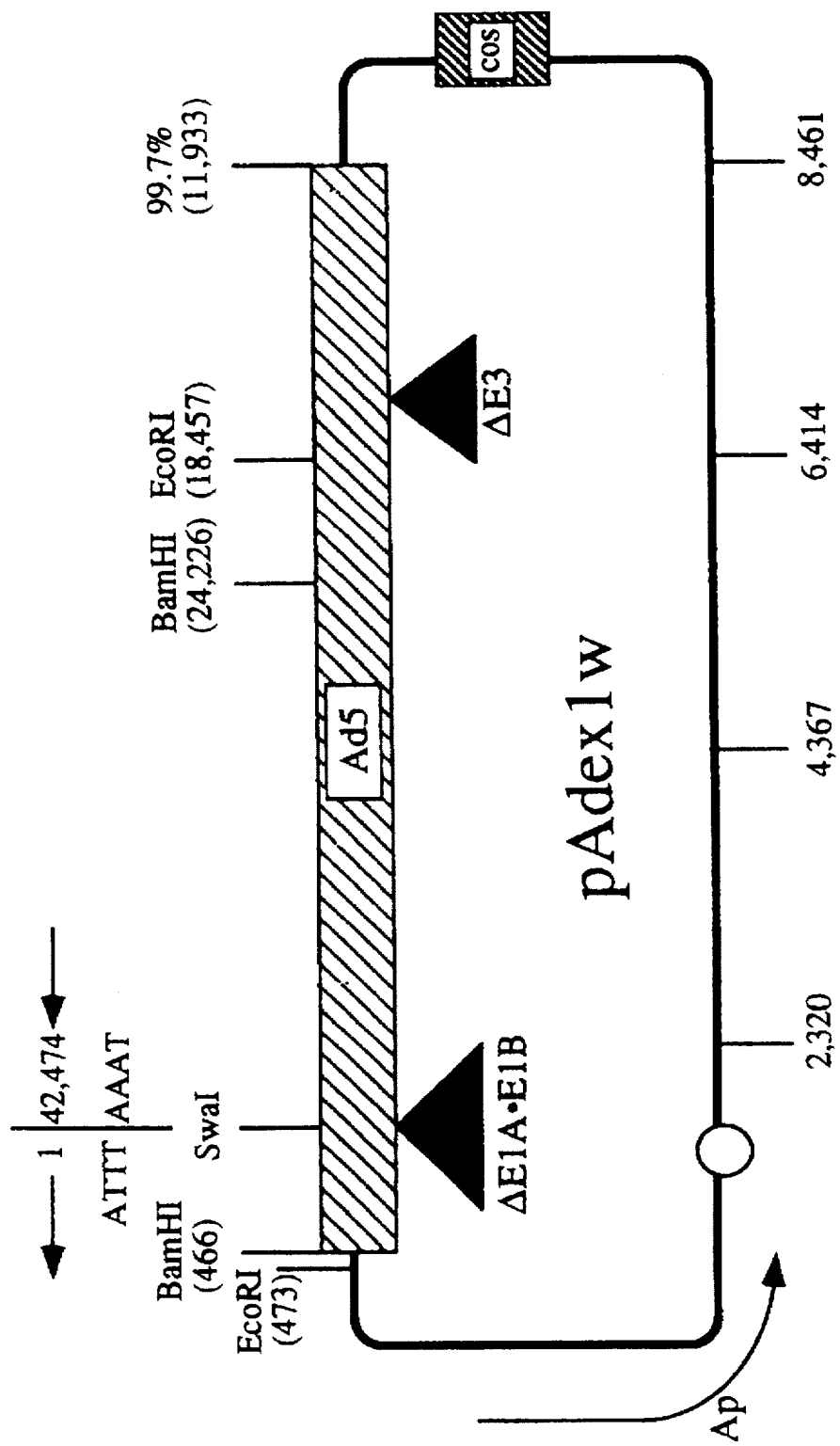
FIG. 2 shows the structure of the pAdexlw.

An adenovirus used in the present invention is a human adenovirus which utilizes a human body as a natural host. The adenoviral genome is a double stranded DNA of about 36 kbp and takes a peculiar structure in that both ends of the DNA strand have an inverted repeat sequence of about 100 bp and that 55 kDa protein which is processed from E2B gene product is covalently bound to the 5' end of each of both ends of the DNA strand. This peculiar structure of the genome has been a serious drawback for a vector as described below. The present invention is characterized by providing a novel and useful recombinant adenovirus and a process for production thereof which have overcome the serious drawback.

The recombinant adenovirus of the present invention is a kind of recombinant vector which is suitable for transfection in an adenovirus-infectious eukaryotic system, particularly in a human or animal cell system. The recombinant adenovirus of the present invention is characterized in that it is deleted of E1 gene region, particularly E1A gene region involving the induction of neoplasm and hence cannot propagate in host cells, except for a cell line constitutively expressing the E1A gene such as a human fetal kidney-derived cell line (293 cell).

When inoculated on the 293 cells, the recombinant adenovirus particles of the present invention can proliferate to a titer level as high as 108 to 109 pfu (plaque forming unit)/ml, similarly to wild strains. When inoculated on other cells or animal tissues, the virus particles of the present invention also invade into cells efficiently and the virus genome is introduced into the nucleus. However, the E1A gene is deleted in the recombinant virus of the present invention so that all adenoviral promoters inherently provided in the virus genome fail to function, because they are activated only in the presence of the E1A gene product. On the other hand, the DNA sequence encoding a desired foreign polypeptide in the recombinant adenovirus of the present invention can be transcribed by the action of the foreign promoter, for example CAG promoter, which is inserted in the adenovirus genome. According to the recombinant adenovirus of the present invention, the foreign gene encoding a desired polypeptide can be expressed ubiquitously in almost all kinds of animal cells, while reducing adverse effects caused by natural adenovirus genomes.

Although cells wherein wild human adenovirus strain can propagate after infection are almost limited to only human cells, the recombinant adenovirus of the present invention can infect and propagate to express the foreign gene in host cells and tissues in a much wider range. This is because the recombinant adenovirus of the present invention can function sufficiently as an expression vector even in hosts wherein a natural adenovirus can not propagate, as far as the virus particles can infect and be internalized into cells.

The genome in the recombinant adenovirus of the present invention is also advantageous as a vector in that, even though the genome is not replicated extrachromosomally, the genome is retained in the nucleus over two weeks to two months to considerably and persistently express the foreign gene.

The genome in the recombinant adenovirus of the present invention is characterized by having a hybrid promoter (CAG promoter) inserted therein comprising a cytomegalovirus enhancer, a chicken β-actin promoter, a rabbit β-globin splicing acceptor and a polyA sequence derived from a rabbit β-globin.

This hybrid promoter (CAG promoter) is disclosed as a high level expression vector in Japanese Patent KOKAI (Laid-Open) No. 3-168087. The hybrid promoter can be prepared by excising from pCAGGS described in Japanese Patent KOKAI supra at page 13, line 20 to page 20, line 14 and page 22, first line to page 25, line 6, with restriction enzymes SalI and HindIII. The hybrid promoter thus produced can be used in the present invention. The present inventors made comparative study on the expression level of lacZ gene with several conventional promoters and found out that the hybrid promoter (CAG promoter) in the recombinant adenovirus is more excellent in the expression level (as shown in Comparative Example hereinafter). Based on the comparative study, the hybrid promoter has been inserted into adenovirus to construct the recombinant adenovirus of the present invention.

The recombinant adenovirus having the hybrid promoter according to the present invention can alleviate side effects which are conventionally observed in human cells infected with a recombinant adenovirus at a high dose in gene therapy. This is because the recombinant adenovirus according to the present invention enables the high level expression of a foreign gene at a low dose.

Any nucleotide sequences may be used, without any particular limitation, as the nucleotide sequence encoding a desired foreign polypeptide sequence which is inserted into the adenovirus genome of the present invention, as long as these sequences are expressed under control of the hybrid promoter (CAG promoter) as described above. In view of therapeutic usefulness, particularly preferred are a DNA sequence which is suspected to be defective in a human gene, a DNA sequence encoding cytokines such as interleukins and interferons, an antioncogene, an antisense sequence of oncogene, and the like.

LacZ gene is also preferred for the gene therapy of gangliosidosis, since LacZ gene expresses β-galactosidase. The nucleotide sequence encoding a desired foreign polypeptide which has been inserted into the recombinant adenovirus of the present invention is expressed under control of CAG promoter in natural host cells to secrete the thus expressed polypeptide into the culture medium.

The genome in the recombinant adenovirus of the present invention is deleted of the E1 gene region, especially the E1A gene region. Thus, the recombinant adenovirus is defective in the E1A gene region which is associated with the neoplastic transformation activity of adenovirus, whereby the recombinant adenovirus according to the present invention is rendered avirulent and only the foreign nucleotide sequence inserted therein is selectively expressed. The entire E1 gene region is not necessarily deleted, but the deletion of the 1.3 to 9.3% segment including the E1A gene region can exhibit the desired effects as stated above. A nucleotide sequence encoding a desired foreign polypeptide and a foreign promoter in the recombinant adenovirus of the present invention are preferably inserted into the E1A -deleted gene region.

Further, the E3 gene region can be also deleted from the genome in the recombinant adenovirus of the present invention. In particular, the deletion of 79.6 to 84.8% segment included in the E3 gene region is preferable. This segment is not required for replication of the foreign nucleotide sequence.

A chicken β-actin promoter which is used to be inserted into the genome of the recombinant adenovirus of the present invention originally exhibits a potent promoter activity without any modifications. The activity is remarkably enhanced by deleting the region from a position in the intron region to the splicing acceptor sequence, and inserting, instead of the thus deleted region, the splicing acceptor sequence derived from a rabbit β-globin structural gene.

As the polyA sequence which is inserted into the genome of the recombinant adenovirus of the present invention, a SV40-derived sequence may be used, and a rabbit β-globin structural gene-derived sequence is preferred.

The genome in the recombinant adenovirus of the present invention has the cytomegalovirus enhancer sequence inserted therein for enhancing the promoter activity of the chicken β-actin promoter.

When the recombinant adenovirus of the present invention thus constructed is infected to animal cells, the recombinant adenovirus genome is transferred into the cells to be stably present extrachromosomally even in nonproliferative cells over a long period of time of from half of a month to two months. Thus, the foreign nucleotide sequence inserted in the genome can continue to express the encoded polypeptide for such a long period of time. In this case, proteins naturally encoded by the genome itself are not expressed and produced due to the deletion of the E1 gene, resulting in that potential side effects associated with adenovirus itself are reduced to a minimum level. It is therefore considered that the recombinant adenovirus of the present invention is extremely useful for gene therapy.

Examples of animal cells to be infected with the recombinant adenovirus are human or mammal lung epithelial cells, gastrointestinal epithelial cells, neuronal cells, liver and muscles (skeletal muscle, heart muscle).

Hereunder, the process for producing the recombinant adenovirus of the present invention is explained in detail.

In general, it is extremely difficult to produce the recombinant adenovirus of the present invention, because proteins are covalently linked to both termini of the adenovirus genome as described hereinabove.

Therefore, the following procedures are preferably used in the present invention.

(1) Firstly, from the entire length of adenoviral genome (36 kb), prepared is a cosmid bearing about 31 kb genomic DNA deleted of the E3 gene region (1.9 kb) and the E1A.E1B gene region (2.9 kb), each of which is not required for replication in 293 cells. To the E1A.E1B-deleted gene region in the cosmid, an expression unit is inserted which contains a foreign promoter, a nucleotide sequence encoding the desired foreign polypeptide to be expressed and a polyA sequence. The expression unit is preferably inserted in an orientation to the left hand.

The cosmid is prepared using lambda in vitro packaging kit, Gigapack XL (Stratagene Co.).

Typical examples of the nucleotide sequence encoding the desired foreign polypeptide to be expressed include nucleotide sequences encoding cytokines such as interleukins 1 through 12, interferon-α, β or γ, tumor necrosis factor-α or β, granulocyte colony stimulating factor, granulocyte macrophage colony stimulating factor, erythropoietin, growth hormone, insulin and insulin like growth factor; a nucleotide sequence encoding adenosine deaminase, dystrophin, neurotrophic factors, thymidine kinase, low density lipoprotein receptor, α-1 antitrypsin, blood coagulation factor VIII, blood coagulation factor IX or galactosidase, each of which would cause genetic diseases when it is defective in human body; allo-HLA (HLA-B7) which is a gene encoding a not-self antigen; a nucleotide sequence encoding a viral antigen; an antioncogene such as p53, RB, WT-1, NM23 or NF-1; anti-Ras sequence which is an antisense of Ras oncogene; and LacZ gene encoding β-galactosidase.

(2) On the other hand, an adenoviral genome is replicated in such a form that proteins encoded by the adenovirus are covalently bound to both ends of the genome. Therefore, the terminal proteins-bound genomic DNA (DNA-terminal protein complex, DNA-TPC) is prepared followed by digestion with restriction enzymes (e.g., EcoT22I, Takara Shuzo Co., Ltd.) for digesting frequently only E1 gene region of the genome or other restriction enzymes including NsiI and AvaIII which have the same recognition site as that of EcoT22I. The thus obtained genome is used as a parent viral genome.

(3) Then the cosmid bearing the desired expression unit as stated above is mixed with the parent viral DNA-TPC followed by transfection to 293 cells (ATCC No. CRL-1573) according to a conventional calcium phosphate co-precipitation method.

In the 293 cells, firstly, homologous recombination occurs in the homologous sequences between the two molecules, i.e., the parent viral DNA and the cosmid. Then, the molecule which has initiated replication from the right end (opposite to the E1 gene region) repairs the left end sequence by cutting off the plasmid sequence utilizing the intact right end sequence. As described above, this is because the adenovirus genome has 102 base pair inverted terminal sequences at both ends thereof, both of which are identical. This mechanism suggests that even if one end of the adenovirus genome is attacked by an exonuclease, the adenovirus genome by itself would repair using the sequence at the other end.

(4) After the foregoing procedures have been conducted, a desired recombinant adenovirus may be collected from the adenovirus propagated in the 293 cells. According to the process of the present invention, any selection markers are not required, because of a high efficiency of generating the desired recombinant adenovirus. The recombinant adenovirus thus isolated may be purified in the following simple manner.

The 293 cells which have been co-transfected with the cosmid bearing the desired expression unit and the digested parent viral DNA-TPC as described above are cultured at 37° C. for about one day. The stock solution, 10-fold dilution and 100-fold dilution of the cultured cells are inoculated on three 96-well plates. From a well containing a single virus only, the virus is isolated and further propagated. From the thus propagated viruses, the desired recombinant adenovirus may be selected.

More specifically, the selection is performed as follows. Each vital solution is infected to the 293 cells to give dead cells due to propagation of the infected virus. From the dead cells, DNA is extracted followed by digestion with restriction enzyme XhoI. The resulting DNA fragments are subjected to electrophoresis to examine the patterns. The adenovirus is selected which exhibits bands including the sequence from the cleavage site in the expression unit of the cosmid to the left end of the adenovirus genome. The solution containing the selected adenovirus may be used as a stock of the desired recombinant adenovirus according to the present invention.

In order to confirm that the solution is not contaminated with either the deleted virus or the parent virus, an aliquot of the solution is infected to the 293 cells to obtain the virus propagated therein, from which DNA is extracted followed by digestion with restriction enzyme XhoI and examination of the resulting digestion patterns. Where the solution is suspected to be contaminated with the deleted virus or the parent virus, the solution is discarded.

In order to make the characteristic features of the present invention clearer, the process of the present invention is compared below with the conventional process according to Melissa A. Rosenfeld et al., Cell vol. 68, 143–155 (1992).

According to the process of the present invention, the cosmid bearing almost the entire length of adenovirus DNA is employed, whereas in the conventional process a cassette of about 5 kb near the E1A.E1B gene region was used. By using such a specific cosmid cassette, the frequency of homologous recombination can be markedly improved in the process of the present invention.

According to the process of the present invention, the terminal proteins-bound genomic DNA (DNA-TPC) is employed as the parent viral DNA, whereas in the conventional process the terminal proteins-deleted DNA was used. This difference results in that the process of the present invention is several tens times more excellent in the efficiency than the conventional process.

In addition, the virus strains obtained in the conventional process have been mostly the parent virus used as a starting material. However, in the present invention, approximately a half of the virus strains obtained are the desired recombinant adenovirus, because restriction enzymes are used which can digest the DNA-TPC at multiple positions (e.g., 3 to 10 positions) in the E1 gene region (left end). Accordingly, in the present invention, any selection markers are not required, unlike the conventional process. Preferred examples of such restriction enzymes are EcoT22I and other restriction enzymes including NsiI and AvaIII which have the same recognition site as that of EcoT22I.

The high titer viral solution thus obtained by the process of the present invention may be effectively used for the treatment of various diseases including hereditary or genetic diseases. After diluted if necessary, the viral solution may be administered through an appropriate route, e.g., topically (central nervous system, portal vein), orally (using enteric coating), by inhalation, subcutaneously, and the like.

Recombinant adenovirus obtained by the process of the present invention may be also effectively used for the expression of foreign genes in in vitro cell culture from various types and species and for the vaccination against human and animals.

Hereinafter, the present invention will be described in more detail by referring to Examples, Reference Examples and Comparative Examples but is not deemed to be limited thereto.

In the Examples, various operations for handling phage, plasmid, DNA, various enzymes, *E. coli*, culture cells and the like were carried out according to the methods as

EXAMPLE 1
Construction of recombinant adenovirus

The recombinant adenovirus is constructed roughly by three steps. That is, the construction comprises the steps of inserting the expression unit into the cosmid, producing the parent virus DNA-TPC and co-transfecting the 293 cells with the cosmid and the DNA-TPC followed by isolation and purification. Each of the steps is explained below in more detail.

(1) insertion of the expression unit into the cosmid
  (i) Firstly, 0.2 μg of an expression unit fragment with blunt ends was mixed with 1 μg of pAdexlw DNA previously digested with SwaI.

In this Example, a set of LacZ gene and the hybrid promoter (CAG promoter) comprising cytomegalovirus enhancer, chicken β-actin promoter, rabbit β-globin splicing acceptor and polyA sequence was used as the expression unit. For making the blunt end, the DNA fragment was treated with Klenow enzyme and completely purified by extractions once with phenol and twice with chloroform and then ethanol precipitation. The expression unit was added in a molar ratio of 2 to 3 times that of the cosmid (44 kb). In general, the presence of SwaI site in an expression unit renders cloning impossible. However, SwaI recognizes eight (8) nucleotides so that the recognition site is rarely present in an expression unit. There was no problem of the expression unit used in this Example.

As the adenovirus construction cassette, pAdexlw was used. After 10 μg of pAdexlw was digested with SwaI, the digestion product was extracted once with phenol and the resulting extract was subjected to centrifugation and gel filtration as described hereinafter. Then, 1 μg each was used. As the cassette cosmid, there may be other cosmids (e.g., pAdex1c) having a ClaI cloning site, in addition to the cosmid (e.g., pAdexlw) having a SwaI cloning site as shown above. Both cosmids are available by using the corresponding restriction enzymes.

(ii) Ethanol was added to the mixture to precipitate DNA. The precipitates were collected by centrifugation and dissolved in 5-fold dilution of a solution (TE:10 mM Tris-HCl (pH 7.5), 1 mM EDTA).
  (iii) The resulting DNA was subjected to ligation overnight in a final volume of 7 μl, by adding ATP and T4 DNA ligase in a buffer solution for a ligase reaction. Sterilized water and a buffer solution for SwaI reaction were added thereto to make the whole volume 48 μl. Then ligase was inactivated with heating at 70° C. for 10 minutes.

Unlike a plasmid, macromolecules of the tandemly-ligated cosmid are much more efficiently packaged in a phage particle than the circularly-ligated molecules.

(iv) After adding 2 μl of SwaI enzyme (Boehringer), digestion was carried out at 25° C. for an hour.

If the cosmid is re-ligated without the insert of the expression unit therein, the SwaI recognition site will be regenerated. The digestion with SwaI is performed to re-cleave the cosmid having no expression unit inserted therein, so that no colony is formed. This is a potential method for selecting only the cosmid having the insert.

(v) The cosmid was subjected to phenol extraction, centrifugation and gel filtration according to a conventional method as described in Molecular Cloning, vol. 3, E.34.
  (vi) Again digestion was performed with SwaI. That is, 5 μl of SwaI enzyme was added to the buffer for the SwaI reaction followed by the cleavage of the cosmid at 25° C. for 2 hours. The cleavage was conducted because of the reason as explained above.
  (vii) In vitro packaging was performed with 1 μl of the resulting cosmid.

That is, lambda in vitro packaging kit, Gigapack XL (Stratagene Co.), was used in a ¼ scale and the rest was frozen at −80° C. The cosmid having become a larger size by including the insert can be selected at a certain extent, since Gigapack XL provides a low package efficiency for a cosmid of 42 kb or less. In this experiment, when 10 colonies were picked up, most of them contained the insert. Therefore, the clone having the desired orientation (i.e., leftward) could be readily obtained.

The cosmid was handled in a conventional manner following the method as described in Izumu Saito et al., JIKKEN IGAKU, vol. 7, 183–187 (1989).

(viii) The packaged cosmid was infected to DH1 (ATCC 33849).

That is, the cosmid was inoculated on three (3) $Ap^+$ (ampicillin-supplemented) agar plates and 5 ml of $Ap^+$ LB (pool), respectively, in amounts of $\frac{1}{200}$, $\frac{1}{20}$, $\frac{1}{2}$ and the rest, followed by incubation overnight.

The miniprep DNA in the pool was extracted and prepared. A ratio of the cosmid having the insert was examined by whole enzymatic digestion. The colony was picked up together with the agar plate and cultured in 1.5 ml of $Ap^+$ LB overnight to prepare the miniprep DNA.

(ix) The orientation and structure of the expression unit inserted were confirmed by digestion with restriction enzymes.

Using NruI and ligase, a plasmid bearing the expression unit but deleted of most adenovirus DNA was prepared, and DNA was then prepared from the plasmid for final confirmation of cDNA cloning. At the same time, the expression of the desired gene, LacZ gene, was confirmed by transient expression in COS cells. As a matter of course, this plasmid was not used but the cosmid was used for producing the recombinant adenovirus.

(2) Production of adenoviral DNA-protein complex (Ad5 d1X DNA-TPC)
  (i) As adenovirus DNA, Ad5 dlX (I. Saito et al., J. Virology, vol. 54, 711–719 (1985)) was used. Ad5 dlX was infected to HeLa cells (at the amount of 10 Roux bottles) followed by incubation.

That is, the vital stock of Ad5-d1X (up to $10^9$ PFU/ml) was infected in 0.2 ml/Roux. Three days after, the detached floating cells were collected by centrifugation at 1500 rpm for 5 minutes. Most of the adenovirus particles were present in the nucleus, but not in the medium. The virus is therefore advantageously purified from the infected cells.

The following procedures were aseptically performed.
  (ii) The thus obtained cells were suspended in 20 ml of 10 mM Tris-HCl (pH 8.0) and sonicated at 200 W for 2 minutes (30 seconds×4) using a sealed type sonicator to release the virus.

In order to release the virus from the cells, when the cell suspension has the volume of 5 ml or less, five repetitions of freeze-thawing are sufficient. However, when having a larger volume, a sonicator is advantageous for releasing the virus.

(iii) After centrifugation at 10 krpm for 10 minutes, the supernatant was collected and overlaid on 15 ml of cesium chloride solution (specific gravity of 1.43)

charged in a ultracentrifuging machine, SW28 tube, followed by concentration with cushion centrifugation (25 krpm, an hour, 4° C.).

(iv) The virus phase immediately beneath the interface was transferred to a SW50.1 tube. The virus phase immediately beneath the interface is generally visually observed; 5 ml of the virus phase and the cesium chloride thereunder were individually collected. At the same time, another tube was filled up with the cesium chloride solution (specific gravity of 1.34).

These tubes were centrifuged at 4° C. overnight at 35 krpm. Then, the thus formed band of virus was fractionated and transferred onto a tube which previously formed gradients. The tube was further subjected to ultracentrifugation at 4° C. for 4 hours at 35 krpm.

(v) The band of virus was fractionated and mixed with an equimolar amount of 8M guanidine hydrochloride. Furthermore, 4M guanidine hydrochloride-saturated cesium chloride was added to the mixture. The resulting mixture was filled in a VTi65 tube. The particle protein was denatured by 4M guanidine hydrochloride to cause dissociation, whereby the DNA-TPC was released. Ethidium bromide could not be used in this experiment, because any procedure for removing the ethidium bromide used has not been established.

(vi) The tube described above was subjected to ultracentrifugation at 15° C. overnight at 55 krpm, followed by fractionation with 0.2 ml. From each of the fractions, 1 µl was mixed and then fluorescence-stained with 1 µg/ml of ethidium bromide aqueous solution to confirm the presence or absence of DNA. Two to three fractions containing DNA were collected.

(vii) The fractions were twice dialyzed against 500 ml of TE overnight. The fraction tubes were then stored at −80° C. The amount of the thus obtained Ad5d1X DNA-TPC was determined by OD260 in the same way as in conventional DNA.

(viii) The resulting Ad5d1X DNA-TPC was digested with a sufficient amount of EcoT22I for 2 hours and then stored at −80° C. for the construction of recombinant adenovirus at the following third steps.

The DNA-TPC could undergo digestion with restriction enzyme, dialysis and gel filtration, but failed to undergo electrophoresis, phenol treatment and ethanol precipitation. The cesium chloride equilibrium centrifugation only is available as a concentration method. Therefore, the system was maintained as dense as possible. Approximately 300 µg of the DNA-TPC could be obtained from infected cells of 10 Roux bottles.

(ix) An aliquot of the solution system was collected and 10 µl of BPB buffer for electrophoresis was added thereto. Then 1 µl of proteinase K (10 mg/ml) was added to the mixture. The resulting mixture was reacted at 37° C. for 10 minutes to digest the terminal proteins on the DNA-TPC. After phenol extraction, the supernatant was separated by agarose gel electrophoresis to confirm complete digestion.

After the restriction enzyme buffer in the EcoT22I-digested DNA-TPC was removed by centrifugation and gel filtration, the products were separately charged in tubes and stored at −80° C.

(3) Isolation of recombinant adenovirus and preparation of high titer viral solution (i) Each one of 6 cm and 10 cm culture dishes charged with the 293 cells cultured in DME supplemented with 10% FCS was prepared.

(ii) After 8 µg (3 to 9 µg is appropriate) of pAdexlW DNA having the expression unit inserted therein was mixed with 1 µg of Ad5d1X DNA-TPC previously digested with EcoT22I, the resulting mixture was transfected to the 293 cells on the 6 cm culture dish using CellPhect transfection Kit (Pharmacia) according to the calcium phosphate method. The mixture was dropped onto the medium in the 6 cm culture dish to continue the incubation.

After the overnight incubation (for about 16 hours), the culture medium was changed in the next morning. Then, in the evening, the medium was poured at 0.1 ml/well with 5% FCS-containing DMA into wells in three 96-well collagen coated plates (stock, 10-fold dilution, 100-fold dilution). In order to avoid a significant difference in the cell number between each plate, a mixture with the 293 cells on the 10 cm culture dish was simultaneously inoculated on plate.

(iii) Three to four days after and eight to ten days after, 50 µl of 10% FCS-containing DME was further added to each well. When the 293 cells became thin, 10% FCS-containing DME was added to the well earlier.

The wells in which the virus propagated and the cells were dead appeared in 7 to 15 days. Every time when the cells in the well were completely dead, each of the culture media was aseptically transferred to a sterilized 1.5 ml tube with a sterile posteur pipette. The tube was quickly frozen and stored at −80° C.

(iv) The judgment was completed in 15 to 18 days. About ten (10) tubes were selected from the tubes in which the cells were dead at a relatively late stage. After six (6) cycles of the freeze-thawing, centrifugation was conducted at 5 krpm for 10 minutes. The resulting supernatant was stored as a first seed at −80° C.

The well in which the virus began to propagate at an earlier stage suggests a higher probability of mixed infection with two or more virus clones.

(v) The 293 cells were charged in a 24-well plate and 5% FCS-DME (0.4 ml/well) and 10−1 of the first vital seed were innoculated to two (2) wells each.

(vi) In about three (3) days, the cells were completely dead; then, the supernatant was obtained from one well by six (6) cycles of freeze-thawing and centrifugation in a manner similar to the procedures for preparing the first viral seed as described above. The thus obtained supernatant was stored at −80° C. for use as a second seed. The titer of the second viral solution was approximately $10^7$ to $10^8$ PFU/ml. The dead cells in another well were centrifuged at 5 krpm for 5 minutes and the supernatant was discarded. The cells alone were stored at −80° C. (cell pack). The cell packs of 10 viral strains were collected and the total DNA was extracted from the infected cells by the following procedures. To each cell pack were added 400 µl of TNE (50 mM Tris-HCl, pH 7.5, 100 mM NaCl, 10 mM EDTA), 4 µl of proteinase K (10 mg/ml) and 4 µl of 10% SDS.

(vii) After treating at 50° C. for an hour, twice extractions with phenol-chloroform, twice extractions with chloroform and then ethanol precipitation gave nucleic acid. The nucleic acid was dissolved in 50 µl of TE containing 20 µg RNase/ml.

After 15 µl of the solution was digested with XhoI containing CG in the recognition site for digesting the expression unit, the digested product was subjected to electrophoresis overnight on agarose gel having a length of about 15 cm. The patterns thus obtained were compared. Selected were the bands exhibiting accurately the sequence from the digested site in the expression unit to the left end (E1 gene region side) of the adenovirus genome. The clones which exhibited an unexpected band were discarded, since there was a possibility that the clones would be contaminated with the virus having deletions.

The adenovirus DNA propagated up to at a level of 10,000 copies/cell. Accordingly, the entire DNA could be extracted together with cell DNA and digested with restriction enzymes to observe the bands of viral DNA. The restriction enzyme such as XhoI containing CG in the recognition site does not digest the cellular DNA and as the result, the pattern could be readily observable. In the case of other enzymes, the non-infected 293 cellular DNA was required for control. The bands derived from human repetitive DNA were observed.

(viii) The second seed stock of the desired virus strain identified by the XhoI digestion, was infected in an amount of 0.1 ml to the 293 cells charged in a 150 cm² collagen-coated bottle containing 25 ml of medium.

In three (3) days the cells were dead and 25 ml of the medium including the dead cells was broken aseptically with a sealed type sonicator at the maximum power of 200 w for 2 minutes (30 seconds×4) to liberate the virus.

The precipitates were removed by centrifugation at 3 krpm for 10 minutes at 4° C., and the obtained supernatant was charged at an amount of 2 ml in each of 13 tubes of 5 ml freezing tube. The tubes were quickly frozen with dry ice and stored at −80° C. to prepare a third seed solution. The third viral seed solution contained the recombinant adenovirus of the present invention which showed a titer as high as $10^9$ PFU/ml.

After infecting 5 μl of the third viral solution to one well of the 293 cells charged in a 24-well plate, the propagated viral DNA was digested with restriction enzymes and the resulting digestion patterns were confirmed by the procedures as described hereinabove. Where there was any doubt that the virus would be a possible mixture with the deleted virus or the parent virus, all of the third seeds were discarded. This is because there would be a possibility that the deleted virus slightly and previously present in the second viral solution rapidly propagated to the predominant level. Therefore, the procedure was again performed with another second seed stock. Alternatively, the desired virus was purified from the first seed solution by a limiting dilution method.

REFERENCE EXAMPLE 1

Simple assay for the titer of the recombinant adenovirus of the present invention The titer of the recombinant adenovirus according to the present invention may be assayed in a simple manner according to the following procedures.

(1) One 10 cm culture dish charged with the 293 cells is prepared.

The recombinant adenovirus solution (i.e., the third seed solution) is serially diluted to $10^{-1}$ to $10^{-4}$ using 5% FCS-supplemented DME, for example, 0.9 ml of DME+0.1 ml of the virus solution. The micropipette tips are all exchanged.

(2) In all wells of one collagen-coated 96-well plate, 5% FCS-supplemented DME is charged by 50 μl each.

On the first row, 25 μl each of the recombinant adenovirus diluted to $10^{-4}$ is charged.

Using a eight (8)-channel pipette, 25 μl is transferred to the wells on the second row. Thereafter the same operation is repeated until the 11th row and the last 25 μl is discarded. As the result, the $3^n$ serial dilutions may be prepared until $3^{11} \times 10^{-4}$. The 12th row is non-infected cells for control.

Micropipette tips used in this case are renewed in every use.

(3) The 293 cells in the 10 cm culture dish are torn off with PBS-EDTA and resuspended in 6 ml of 5% FCS-supplemented DME. The cell suspension is charged in the 96 wells by 50 μl each.

Three to four days after and six to seven days after, 50 μl of 10% FCS-supplemented DME is gently charged to each well, using a sterile micropipette tip for "cell-saver".

Twelve (12) days after, the endpoint of the cytopathic effect is microscopically observed. Where the cells are maintained until fourteen days after, the judgement is quite easily conducted. However, where the cells are damaged, the judgement becomes difficult.

The median tissue culture infection dose ($TCID_{50}$) is determined statistically according to the Gelber equation (1):

Where $TCID_{50}$ to be determined is made 10×, X=log a⁻ (the number of denatured well at each dilution stage/the total number of the samples at each dilution stage—0.5)×log (dilution magnification)  (1)

wherein the symbol "a" represents dilution magnification (in this protocol, $10^{-4} \times 3^{-1}$)

Experiment

The cytopathic endpoint was microscopically determined twelve (12) days after. The results obtained are shown in Table 1. In this case, the titer was assayed as follows:

The volume of the diluted virus solution was 50 μl. When the titer was 1 PFU in 50 μl at this concentration, the titer of the viral stock was:

$$1 \text{ ml} + 50 \text{ μl} - 10^{-7.817} = 20 \times 10^{7.817}$$
$$= 10^{9.118}$$
$$= 1.3 \times 10^9 \, (PFU/\text{ml})$$

That is, when a half of the 8th row showed cytopathic effects, the titer was $1.3 \times 10^9$ PFU/ml and when cytopathic effects occurred up to a half of the 7th row, the titer reached ⅓ of the above titer, that is, $4.4 \times 10^8$ PFU/ml.

TABLE 1

| | 1<br>$10^{-4} \times$<br>$3^{-1}$ | 2<br>$10^{-4} \times$<br>$3^{-2}$ | 3<br>$10^{-4} \times$<br>$3^{-3}$ | 4<br>$10^{-4} \times$<br>$3^{-4}$ | 5<br>$10^{-4} \times$<br>$3^{-5}$ | 6<br>$10^{-4} \times$<br>$3^{-6}$ | 7<br>$10^{-4} \times$<br>$3^{-7}$ | 8<br>$10^{-4} \times$<br>$3^{-8}$ | 9<br>$10^{-4} \times$<br>$3^{-9}$ | 10<br>$10^{-4} \times$<br>$3^{-10}$ | 11<br>$10^{-4} \times$<br>$3^{-11}$ | 12<br>0 |
|---|---|---|---|---|---|---|---|---|---|---|---|---|
| A | ○ | ○ | ○ | ○ | ○ | ○ | ○ | ○ | ● | ● | ● | ● |
| B | ○ | ○ | ○ | ○ | ○ | ○ | ○ | ● | ● | ● | ● | ● |
| C | ○ | ○ | ○ | ○ | ○ | ○ | ○ | ● | ● | ● | ● | ● |
| D | ○ | ○ | ○ | ○ | ○ | ○ | ○ | ● | ● | ● | ● | ● |
| E | ○ | ○ | ○ | ○ | ○ | ○ | ○ | ○ | ● | ● | ● | ● |
| F | ○ | ○ | ○ | ○ | ○ | ○ | ○ | ● | ⊙ | ● | ● | ● |
| G | ○ | ○ | ○ | ○ | ○ | ○ | ● | ● | ● | ● | ● | ● |

TABLE 1-continued

| | 1<br>$10^{-4} \times$<br>$3^{-1}$ | 2<br>$10^{-4} \times$<br>$3^{-2}$ | 3<br>$10^{-4} \times$<br>$3^{-3}$ | 4<br>$10^{-4} \times$<br>$3^{-4}$ | 5<br>$10^{-4} \times$<br>$3^{-5}$ | 6<br>$10^{-4} \times$<br>$3^{-6}$ | 7<br>$10^{-4} \times$<br>$3^{-7}$ | 8<br>$10^{-4} \times$<br>$3^{-8}$ | 9<br>$10^{-4} \times$<br>$3^{-9}$ | 10<br>$10^{-4} \times$<br>$3^{-10}$ | 11<br>$10^{-4} \times$<br>$3^{-11}$ | 12<br>0 |
|---|---|---|---|---|---|---|---|---|---|---|---|---|
| H | ○ | ○ | ○ | ○ | ○ | ○ | ○ | ○ | ● | ● | ● | ● |
| Number of the positives of cytopathic effects | 8 | 8 | 8 | 8 | 8 | 8 | 7 | 4 | 1 | 0 | 0 | |

●: no cytopathic effect by the virus, or less than 50%
○: cytopathic effect of 50% or more by the virus
⊙: ineffective where the cytopathic effect sporadically appears on the dilution series

REFERENCE EXAMPLE 2
Construction of pAdex1c and pAdex1w

We prepared cosmid, pAdex1c, in the following manner.
(1) Preparation of pUAF0-17D which contains left terminal 17% fragment of adenovirus genome with deletion of E1 gene region.

Adenovirus type 5 DNA treated with S1 nuclease and rendered blunt-end fragment was purified by phenol extraction and ethanol precipitation. The blunt-end fragment was ligated with BamHI linker. The ligated fragment was digested with HindIII and DNA sample was separated by electrophoresis in agarose gel. The fragment of 2.8 kb size (left terminal 8% fragment of Adenovirus genome) was recovered by electroelution from gel slices and inserted into BamHI/HindIII digested pUC19. Resulting plasmid was named pUAF0-8.

Adenovirus type 5 DNA was digested with HindIII and DNA sample was applied on the agarose gel electrophoresis. The fragment of 3.4 kb size (8–17% fragment of Adenovirus genome) was recovered and inserted into HindIII digested pUC19. Resulting plasmid was named pUAF8-17.

The PvuII site at nucleotide position 454 in pUAF0-8 was converted to a ClaI site by using ClaI linker. Then, the DNA sample was digested with Bam HI/ClaI and the resulting Bam Hi-ClaI fragment (454 nucleotide(nt)) was purified through the agarose gel electrophoresis.

The BglII site at nucleotide position 3328 in pUAF8-17 was converted to a ClaI site by using ClaI linker. Then, the DNA sample was digested with BamHI/ClaI and the resulting BamHI-ClaI fragment (2.9 kb) was purified through the agarose gel electrophoresis.

The BamHI-ClaI fragment (454 nt) from pUAF0-8 and the BamHI-ClaI fragment (2.9 kb) from pUAF8-17 were ligated and inserted into BamHI/HindIII digested pUC19. Resulting plasmid was named pUAF0-17D which contains 0–17% fragment of adenovirus genome with deletion of E1 gene region.

(2) Preparation of Bst1107-EcoRI fragment (21.6 kb) of adenovirus genome.

Adenovirus type 5 DNA was digested with Bst1107 and EcoRI and DNA sample was applied on agarose gel electrophoresis. The fragment of 26.6 kb size was purified from the gel.

(3) Preparation of EcoRI-SalI fragment (6.5 kb) of adenovirus genome.

pX2W was constructed from pX2S (I. Saito et. al., J. of Virology, vol. 54, p711–719, 1985) by inserting SwaI linker at the SalI site. It was digested with EcoRI and SwaI and DNA sample was applied on agarose gel electrophoresis. The fragment of 6.5 kb size was purified from the gel.

(4) Preparation of charomid (chdRBR7-11)

To delete KpnI, SmaI and BamHI sites in charomid9-11 (I. Saito & G. Stark, Proc. Natl. Acad. Sci., vol. 83, p8664–8668, 1986), charomid9-11 was digested with Asp718 and BamHI, filled in by Klenow fragment of DNA polymerase I. and self-ligated.

After transformation, the resulting charomid was named charomid6-11 which lacks KpnI, SmaI and BamHI sites.

New BamHI site was regenerated by using BamHI linker at EcoRI site (EcoRI site also regenerated). The resulting charomid was named chdRBR7-11.

(5) Preparation of pAdex1c

To construct pAdex1c, the BamHI-Bst1107 fragment (2.9 kb) of pUAF0-17D, the Bst1107-EcoRI fragment (21.6 kb) of adenovirus genome, the EcoRI-SwaI fragment (6.5 kb) of pX2W and the EcoRI/Ecl36I digested chdRBR7-11 were ligated. After ligation, the reaction mixture was packaged in vitro and adsorbed to DH5α cells. pAdex1c was selected from transformants.

(6) Preparation of pAdex1w pAdex1w was constructed from pAdex1c by converting the ClaI site to SwaI site.

COMPARATIVE EXAMPLE 1
Influence of various promoters on expression of LacZ gene for various established cell lines Recombinant adenoviruses were prepared by substituting SRα promoter (SV40 early promoter+ HTLV13'LTR) or EF-1α promoter (derived from human polypeptide elongation factor gene) for the promoter (CAG promoter) in the recombinant adenovirus of the present invention, and compared with the recombinant adenovirus of the present invention in the activity for expressing LacZ gene.

SRα promoter is disclosed in Takebe et al., Molecular and Cellular Biology, vol. 8, 466–472, 1991. EF-1α promoter is disclosed in Kim et al., Gene, vol. 91, 217–223, 1990.

The expression unit was inserted into the recombinant adenovirus genome in the following manner.

(1) In order to insert CAG promoter and LacZ gene into the adenovirus genome, LacZ gene was firstly inserted into pCAGGS. That is, pCAGGS was digested with EcoRI and rendered blunt end with Klenow fragment. The SwaI linker was inserted into this digested site. On the other hand, pMC1871 (Shapiro et al., Gene, vol. 25, 71–82, 1983) was used as a material for LacZ gene. In LacZ of pMC1871, the nucleotide sequence encoding N-terminal seven (7) amino acids which is unnecessary for LacZ activity forms a polylinker sequence. The nucleotide sequence was digested with SmaI followed by ligation with NotI linker, and then with synthetic DNA bearing an initiation codon, namely, (PstI end)-CAGACCGTGCATCATGA-(NotI end) (SEQ ID NO:1). After cleaving PstI site downstream of a termination codon, the thus formed end was rendered blunt and inserted into the SwaI site in pAGGS as described above. Thus, a plasmid having LacZ gene downstream of CAG promoter was obtained. Then, the plasmid was digested with SalI and HindIII and the resulting fragment was blut-ended.

The plasmid was ligated with pAdex1w previously digested with SwaI to prepare an expression cosmid. The adenovirus which contains the expression unit having an orientation to the left hand was selected and used for constructing the recombinant adenovirus.

(2) For the insertion of SRα promoter and LacZ gene into the adenovirus genome, pMC1871 was used as a material for LacZ gene in the same way as in the CAG promoter. After digesting with SmaI at the 5' end, NotI linker was ligated and then digested with PstI downstream of a termination codon. The ends were rendered blunt and then ligated with KpnI linker. The LacZ fragment was ligated with the synthetic DNA as described above to be cloned between the PstI site and the KpnI site of the expression vector pcDL-SRα296 bearing SRα promoter (pSRLacZ).

To prepare the recombinant adenovirus (Adex1SRLacZ) for expressing LacZ under control of SRα promoter, the expression unit of SRα-LacZ-polyA was excised from pSRLacZ using HindIII and TthIIII and rendered blunt. The expression unit was then inserted into Adex-producing cassette, AdexlW, at the SwaI site. The adenovirus which contains the expression unit having an orientation to the left hand was selected and used for constructing the recombinant adenovirus.

(3) The recombinant virus for expressing LacZ under control of EF1α promoter was prepared as follows: The SV40 T antigen region was first deleted from expression vector pEF321-T (Kim et al., Gene, vol. 91, 217–223, 1990) using HindIII and HpaI and linked with SwaI synthetic linker to construct pEF321w. The region containing the initiation codon in pSRLacZ was excised with PstI and KpnI, and then rendered blunt end, followed by insertion into the SwaI site in pEF321w to prepare pEFLacZ. The expression unit of EFIα-LacZ-polyA was excised from pEFLacZ with NheI and KpnI and inserted into the SwaI site in pAdex1w. The adenovirus which contains the expression unit having an orientation to the left hand was selected and used for constructing the recombinant adenovirus.

The established cell lines to be infected were HeLa cells, HepG2 cells, IMR-32 cells, EB (Epstein-Barr virus) transformed B cell-clone 1, EB transformed B cell-clone 2, Jurkat cells, CV-1 cells, CRFK cells, MYA-1 cells, SHOK cells, NIH3T3 cells, Ltk- cells, and Ba/F3 cells.

The activity of β-galactosidase expressed was assayed as follows:

The $3 \times 10^5$ cells were cultured in each well of a 24-well plate and the recombinant adenovirus constructed was infected thereto at m.o.i. (multiplicity of infection) of 10. After incubation for two (2) days, the cells were collected in an Eppendorf's tube and washed twice with PBS. Then 0.5 ml of buffer for extraction was added thereto. After ultrasonication with 30 second intervals for 90 seconds in total, 0.5 ml of 80% glycerol was added and the resulting mixture was centrifuged at 15000 rpm for 10 minutes. The thus obtained supernatant was used as the cell extract.

To 850 μl of a reaction mixture containing 1.0 ml of 0.5M sodium phosphate buffer (pH 7.8), 1.0 ml of 0.5M β-mercaptanol, 1.0 ml of 10 mM MgCl$_2$ and 5.5 ml of distilled water was added 50 μl of the cell extract, the cell extract buffer (for blank control) or β-galactosidase solution (for control), followed by preincubation for 5 minutes. Then, a substrate solution was further added thereto. As the substrate, o-nitrophenyl-β-galactoside was used.

After incubation for 30 minutes, 400 μl of a reaction-terminating solution was added and absorbance was measured at 420 nm. The activity was determined according to the following equation.

Where absorbance exceeds 1, it is preferred that the cell extract solution is diluted with extraction buffer and the absorbance is again measured. Units/ml= (absorbance of sample—absorbance of blank)/$4.51^a$)×1.4 ml$^b$)×1/30 min$^c$) ×1.0 ml/0.05 ml$^d$) wherein:

a): The concentration μmole/ml of the enzyme reaction product is determined by dividing with extinction coefficient of o-nitrophenol, i.e., absorbance of 1 mM aqueous solution.

b): The amount μmole of the reaction product is determined by multiplying the volume after the reaction was terminated.

c): The amount μmole of reaction product per minute is determined by dividing with the reaction time.

d): The volume of the enzyme solution provided for the reaction is for converting into the reaction amount per 0.05 ml and 1 ml.

The results obtained are shown in FIG. 1. The results reveal that the CAG promoter in the present invention exhibits a much more potent expression activity in all the cells tested, than in SRα promoter and EF-1α promoter.

One unit was defined to be a catalytic amount which hydrolyzes 1 μmole of o-nitrophenyl-β-galactoside into o-nitrophenol and D-galactose for one minute under the conditions described above.

According to the present invention, the recombinant adenovirus which effectively expresses a gene in a wide range of animal cells is advantageously provided. The present invention also provides a simple process for producing the recombinant adenovirus. The recombinant adenovirus of the present invention is effective for the treatment of genetic diseases.

COMPARATIVE EXAMPLE 2

Influence of orientation on expression of LacZ and HCV gene for various promoters. Recombinant adenoviruses having different promoters and genes in opposite orientations were prepared, and compared with each other in the activity for virus production.

(1) Construction of HCV expressing recombinant adenovirus

The cDNA fragment of 2.2 kb size (nucleotide number; 307–2554) was isolated by polymerase chain reaction and was inserted between the PstI and the KpnI site of the pcDL-SRα296 in the same manner of LacZ cDNA.

Recombinant adenovirus was also prepared in a similar way.

(2) Construction of LacZ expressing recombinant adenovirus

The preparation was as same as Comparative Example 1.

The results obtained are shown in Table 2. The results reveal that the leftward in the present invention exhibits a much more potent production activity in three cases, than in rightward.

TABLE 2

Virus titer of recombinant adenovirus having different promoters and genes in opposite orientations.

| Vector | Virus titer/ml | Promoter/Gene |
|---|---|---|
| SRLacZL | $1.3 \times 10^9$ | SRα promoter + LacZ |
| SRLacZR | $1.1 \times 10^9$ | |
| EFLacZL | $4 \times 10^8$ | EF1α promoter + LacZ |
| EFLacZR | $6 \times 10^7$ | |
| CALacZL | $3 \times 10^8$ | CAG promoter + LacZ |
| CALacZR | $2 \times 10^7$ | |
| SR325L | $1 \times 10^9$ | SRα Promoter + HCV structural genes |
| SR325R | $1 \times 10^8$ | |

L: leftward orientation
R: Rightward orientation

What is claimed is:

1. A process for producing a recombinant adenovirus having an expression unit inserted in an adenovirus genome comprising the steps of:
   (a) constructing an adenovirus cosmid wherein said adenovirus cosmid is deleted of at least the E1A gene of the E1 gene region and inserting the expression unit into the E1A-deleted gene region
   (b) digesting an adenovirus DNA-terminal protein complex with a restriction enzyme at 3 to 10 sites an the left-hand side of the adenovirus genome;
   (c) co-transfecting a cell line which expresses an E1A gene with the cosmid obtained in step (a) and the adenovirus DNA-terminal protein complex obtained in step (b); and
   (d) producing a recombinant adenovirus having an expression unit inserted into the adenovirus genome.

2. The process according to claim 1, wherein said cell line is a human fetal kidney-derived cell line.

3. The process according to claim 1, wherein said expression unit comprises a nucleotide sequence encoding a desired foreign polypeptide and a CAG promoter comprising a cytomegalovirus enhancer, a chicken β-actin promoter, a rabbit β-globin splicing acceptor and a polyA sequence.

4. The process according to claim 1, wherein said restriction enzyme is EcoT22I, NsiI or AvaIII, wherein NsiI and AvaIII both have the same recognition site as that of EcoT22I.

5. The process according to claim 1, wherein said expression unit is inserted into the genome in an orientation of transcription to the left-hand which is opposite to an orientation of E1A gene transcription.

6. The process according to claim 1, wherein the E3 gene of the adenovirus genome is deleted in said cosmid and said adenovirus DNA-terminal protein complex.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:1:

CAGACCGTGC ATCATGA    17